US005405956A

United States Patent [19]

Hay et al.

[11] Patent Number: 5,405,956

[45] Date of Patent: Apr. 11, 1995

[54] CYCLIC OLIGOMERS FOR PRODUCTION OF LINEAR POLYKETONES, POLYPHTHALAZINES AND POLYISOQUINOLINES

[76] Inventors: Allan S. Hay, 5015 Glencairn Avenue, Montreal, Quebec H3W 2B3; Kwok P. Chan, 3512 Durocher Avenue, Apt. #305, Montreal, Quebec H3X 2E6, both of Canada

[21] Appl. No.: 204,065

[22] Filed: Mar. 1, 1994

[51] Int. Cl.$^6$ .............................................. C07D 498/00

[52] U.S. Cl. .......................................... 540/469; 568/31; 568/337; 528/126; 528/171; 528/174; 528/226; 528/229; 528/176; 528/179; 528/225

[58] Field of Search .................... 540/224; 568/31, 337

[56] References Cited

U.S. PATENT DOCUMENTS

| | | | |
|---|---|---|---|
| 4,959,454 | 9/1990 | Fukuyama | 528/352 |
| 5,107,029 | 4/1992 | Walker, Jr. et al. | 568/319 |
| 5,264,520 | 11/1993 | Mullins et al. | 528/125 |
| 5,264,538 | 11/1993 | Mullins et al. | 528/226 |
| 5,306,789 | 4/1994 | Hay et al. | 525/471 |
| 5,338,881 | 8/1994 | Walker, Jr. et al. | 562/462 |

OTHER PUBLICATIONS

Concise Encyclopedia of Polymer Science and Engineering, J. I. Kroschwitz pp. 1006–1008, John Wiley & Sons.

Opening Rings to Polyethers, Mullins et al, American Chemical Society, 1003, Chemtech Aug. 1993, pp. 25–28.

*Primary Examiner*—John Kight, III
*Assistant Examiner*—Shelley A. Dodson
*Attorney, Agent, or Firm*—Bachman & LaPointe

[57] ABSTRACT

Low molecular weight cyclic oligomers of formula (I)

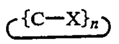

(I)

in which n is an integer of 2 to 20, and each C in the oligomer is a radical of formula (II):

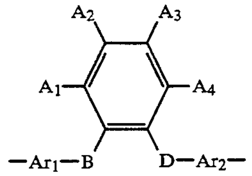

(II)

and each X in the oligomer is —O—R—O— or —S—R—S—, B and D are both carbonyl groups CO, or together represent a divalent radical of formula $$—C=N—N=C— \qquad (III)$$

or

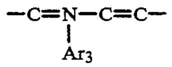

(IV)

in which $A_1$, $A_2$, $A_3$ $A_4$, $Ar_1$, $Ar_2$ and $Ar_3$ are selected from a variety of aromatic radicals, $A_1$, $A_2$, $Ar_3$ and $Ar_4$ also possibly being hydrogen, are useful in the production of high molecular weight, linear, polyketones, polyphthalazines and polyisoquinolines; the cyclic oligomers have low melt viscosities when heated above their softening temperatures and can be readily molded, whereafter they can be rings-open polymerized to form molded high molecular weight polymer products with excellent properties.

16 Claims, No Drawings

CYCLIC OLIGOMERS FOR PRODUCTION OF LINEAR POLYKETONES, POLYPHTHALAZINES AND POLYISOQUINOLINES

BACKGROUND OF THE INVENTION

1. Field of the Invention

This invention relates to cyclic oligomers and a process for their preparation; the invention also relates to the use of the cyclic oligomers for the production of high molecular weight, linear polymers.

2. Description of Prior Art

High temperature polymers which are of high molecular. weight are difficult, if not impossible in many cases, to process in the melt because of their high melt viscosities at the elevated temperatures that would be required. Cyclic monomers and oligomers, since they are low molecular weight materials, have very low melt viscosities when heated which permits their fabrication into a desired shape whereafter they can be polymerized in situ to give the fabricated product.

Generally polymers of much higher molecular weight can be prepared from cyclics than in a conventional condensation polymerization reaction where the viscosity of the reaction mixture (solution or melt) limits the conversion in the polymerization reaction. Cyclic monomers and oligomers are thus potentially very important for the fabrication of advanced composites which contain large volume fractions of carbon fibers where precise alignment of the fibers is required to attain optimum properties, and for high performance adhesives since the cyclic materials can wet surfaces thoroughly and can then be polymerized in situ to give excellent bonding. Furthermore, the systems can often be designed so that the polymerized cyclic is cross-linked which offers further increases in temperature capability and also results in increased solvent resistance in the fabricated product.

A recent article ("Opening Rings to Polyethers" Chemtech, August, 1993, pp 25–28, by M. J. Mullins, E. P. Woo, D. J. Murray and M. T. Bishop) summarizes recent effects in the synthesis of cyclic oligomers of poly(aryl ether)s and methods to polymerize them with catalysts by a nucleophilic polymerization reaction.

Cyclic polycarbonate oligomers have been synthesized and it has been shown that they can be polymerized in situ to high molecular weight polycarbonates in the presence of a catalyst. (See U.S. Pat. Nos. 4,644,053; 4,696,998 and 4,727,134; also described in Polymer Preprints, American Chemical Society 30 (#2), 569, 571, 575, 577, 579, 581.) Mixtures of cyclics with linear polymers are obtained, which generally have to be separated, with yields of the cyclics being as high as 85%.

When spirobiindane bisphenols (SBI) are used higher yields of the cyclics are obtained so that often the cyclics can be used without separation of the linear polymer fraction. The rigid conformation of the SBI favors the formation of the cyclic. However, on polymerization residual amounts of the cyclics are retained because of the favorable ring-chain equilibrium (D. J. Brunelle, T. L. Evans and T. G. Shannon, U.S. Pat. No. 4,736,016, Apr. 5, 1988).

Cyclic poly(aryl ether) oligomers have also been synthesized in good yields along with the linear polymers (Mullins et al, above); (M. J. Mullins et al, U.S. Pat. No. 5,264,520; M. J. Mullins et al, U.S. Pat. No. 5,264,538). Using SBI as the bisphenol, cyclic poly(ether ketone)s and poly(ether sulfone)s have been synthesized in high yields. (J. M. Fukuyama, U.S. Pat. Nos. 4,959,454 and 5,110,893.)

Recently poly(ether ketone)s have been synthesized from the reaction of bisphenols with ortho-bis(4-fluoro- or 4-chlorobenzoyl)benzenes (A. S. Hay and R. Singh, U.S. Ser. No. 606,160, filed Oct. 31, 1990; R. Singh and A. S. Hay, Macromolecules 24, 2637–39 (1991); 24, 2640–42 (1991); 24, 2643–46 (1991)). These polymers are amorphous and have very high glass transition temperatures which increase with the number of pendant phenyl groups on the central benzene ring. The polymers can be converted to the corresponding phthalazines and isoquinolines by reaction with hydrazine and benzylamine, respectively. This conversion results in an increase in the solution viscosity as well as the glass transition temperature since the conversion results in a straightening of the chain and a resulting increase in the end-to-end distance as well as the rigidity of the polymer chain.

SUMMARY OF THE INVENTION

It is an object of this invention to provide cyclic oligomers useful in the manufacture of high molecular weight linear polymers.

It is a further object of this invention to provide a process for the production of the cyclic oligomers.

It is a still further object of this invention to provide a process for the production of high molecular weight linear polymers from the cyclic oligomers.

In accordance with the invention in one aspect there is provided cyclic oligomer of formula (I):

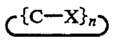

(I)

wherein n is an integer of 2 to 20 and in which each C in the oligomer is a radical of formula (II):

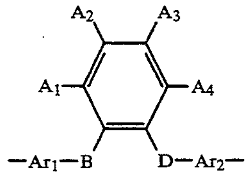

(II)

and each X in the oligomer is —O—R—O— or —S—R—S—, in which $A_1$, $A_2$, $A_3$ and $A_4$ are each independently selected from hydrogen, aryl selected from the group consisting of phenyl, naphthyl and anthracyl, diphenylether or heteroaromatic radicals selected from the group consisting of pyridinyl, pyrazinyl, quinolinyl, thiophenyl, benzothiophenyl, furanyl and dibenzofuranyl, said aryl, diphenylether and heteroaromatic radicals being unsubstituted or substituted by a substituent selected from lower alkyl of 1 to 6 carbon atoms, lower alkoxy of 1 to 6 carbon atoms, lower thioalkyl of 1 to 6 carbon atoms, halogen, phenyl, naphthyl, anthracyl, diphenylether or heteroaromatic radicals selected from the group consisting of pyridinyl, pyrazinyl, quinovlinyl, thiophenyl, benzothiophenyl, furanyl and dibenzofuranyl, B and D are both carbonyl groups CO, or B and D together represent a divalent radical of formula:

$$—C{=}N—N{=}C— \quad (III)$$

-continued or

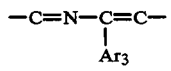

(IV)

wherein $Ar_3$ is an aryl selected from the group consisting of phenyl, naphthyl and anthracyl, diphenylether or heteroaromatic radical selected from the group consisting of pyridinyl, pyrazinyl, quinolinyl, thiophenyl, benzothiophenyl, furanyl and dibenzofuranyl, unsubstituted or substituted by a substituent selected from lower alkyl of 1 to 6 carbon atoms, lower alkoxy of 1 to 6 carbon atoms, lower thioalkyl of 1 to 6 carbon atoms, halogen, phenyl, naphthyl, anthracyl, diphenylether or heteroaromatic radicals selected from the group consisting of pyridinyl, pyrazinyl, quinolinyl, thiophenyl, benzothiophenyl, furanyl and dibenzofuranyl, $Ar_1$ and $Ar_2$ are each phenylene radicals, unsubstituted or substituted 1 to 4times by a substituent selected from lower alkyl of 1 to 6 carbon atoms, lower alkoxy of 1 to 6 carbon atoms, lower thioalkyl of 1 to 6 carbon atoms, halogen, phenyl, naphthyl, anthracyl, diphenylether or heteroaromatic radicals selected from the group consisting of pyridinyl, pyrazinyl, quinolinyl, thiophenyl, benzothiophenyl, furanyl and dibenzofuranyl, R is arylene selected from the group consisting of phenylene, naphthylene, anthracylene, thiobisphenyl, sulfonylbisphenyl and alkylidinylbisphenyl of formula $$—Ph—R_1—Ph—$$

which $R_1$ is a straight chain or branched alkylene of 1 to 6 carbon atoms and Ph is phenylene, in which each arylene and phenylene moiety is unsubstituted or substituted by lower alkyl of 1 to 6 carbon atoms, lower alkoxy of 1 to 6 carbon atoms, lower thioalkyl of 1 to 6 carbon atoms, halogen, phenyl, naphthyl, anthracyl, diphenylether or heteroaromatic radicals selected from the group consisting of pyridinyl, pyrazinyl, quinolinyl, thiophenyl, benzothiophenyl, furanyl and dibenzofuranyl, and the alkylidine moiety of said aralkylidinylphenyl is unsubstituted or fluoro-substituted alkylidine.

When B and D are both carbonyl groups, the oligomer is a cyclic polyketone oligomer.

When B and D represent the divalent radical of formula (III), whereby B and D form part of a pyridazine ring, the oligomer is a cyclic polyphthalazine oligomer.

When B and D represent a divalent radical of formula (IV), whereby B and D form part of a pyridine ring, the oligomer is a cyclic polyisoquinoline oligomer.

In another aspect of the invention there is provided a process for the preparation of a linear, high molecular weight polymer which comprises the ring-open polymerization of a cyclic oligomer of formula (I), as defined hereinbefore, at an elevated temperature in the presence of a catalyst.

In yet another aspect of the invention there is provided a process for producing a cyclic oligomer of formula (I), as defined hereinbefore which comprises reacting a di-carbonyl compound of formula (V):

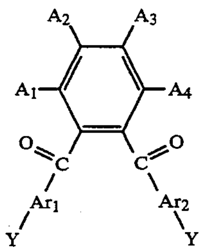

with a compound of formula (VI)

$$HZ—R—ZH \quad (VI)$$

in a solvent under high dilution conditions such that reactive end groups Y and ZH are present in a low concentration, to produce a cyclic oligomer of formula (I), in which B and D are both carbonyl groups, and in which $A_1$, $A_2$, $A_3$, $A_4$, $Ar_1$, $Ar_2$ and R are as defined hereinbefore, each Y is chloro or fluoro and each Z is O or S.

In accordance with still another aspect of the invention there is provided a process for producing a cyclic polyphthalazine of formula (I), in which B and D represent the divalent radical of formula (III) whereby B and D form part of a pyridazine ring which comprises reacting a corresponding cyclic polyketone oligomer of formula (I) with hydrazine.

In accordance with a Still further aspect of the invention there is provided a process for producing a cyclic polyisoquinoline of formula (I) in which B and D represent said divalent radical of formula (IV) whereby B and D form part of a pyridine ring, which comprises reacting a corresponding cyclic polyketone oligomer of formula (I) with benzylamine.

DESCRIPTION OF PREFERRED EMBODIMENTS i) Oligomer Formation

It has been found that if the reaction of the dicarbonyl compound (V) with the compound (VI) is carried out in a solvent under high dilution conditions, the cyclic oligomer (I) is formed essentially quantitatively. In contrast to previous examples cited since only small amounts or no iinear oligomers or polymers are formed, separation processes are not required. Thus it is a particular advantage of the invention that the reaction mixture containing the product cyclic oligomer (I) can be employed directly for polymer manufacture without the necessity of isolating the cyclic oligomer (I). It was particularly suprising that the cyclic oligomers were produced in high yield with only small amounts or no by-product linear polymers, since prior processes produce significant quantities of by-product linear polymers which need to be removed prior to the ring-opening polymerization of the cyclic oligomer, and and which reduce the yield of final polymer.

At high dilution of the reactants, the reactive end groups of the dicarbanoyl compound (V) and the compound (VI), i.e., Y and ZH are present in low concentrations so that the cyclic oligomers are the kinetically favoured reaction products.

The reaction is carried out at low reaction temperatures, typically of the order of 100° C. to 140° C.; higher temperatures encourage formation of non-cyclic, linear polymeric species.

Suitable solvents include dimethyl formamide and toluene, and the reaction is suitably carried out in the presence of a base, for example, an alkali metal carbonate, such as potassium carbonate.

The high dilution conditions can be achieved by adding the reactants (V) and (VI) portionwise over a period of time, to the solvent containing the base and heating the reaction mixture.

Using solvent combinations of low boiling point the process may be carried out under reflux conditions.

The resulting cyclic oligomers are of low molecular weight and have low melt viscosities above their softening temperatures and can thus be molded into desired shapes. Thereafter the cyclic oligomers can be ring-open polymerized to linear, high molecular weight polymers with excellent properties, which polymers can not themselves be readily molded, in view of their high softening and melting temperatures.

Typically the oligomers of the invention may have a molecular weight of 1,000 to 15,000 and a softening temperature of 250° C. to 350° C., and may be employed to produce linear, high molecular weight polymers having a molecular weight above 100,000.

The ring-opening polymerization of the cyclic oligomers may be carried out in a solvent, which may be the solvent employed in the production of the cyclic oligomer; or may be carried out in a melt of the oligomer.

The ring-opening polymerization is suitably carried out in the presence of a catalyst, suitable catalysts include alkali metal fluorides, for example, cesium fluoride, phenoxides, for example, potassium, phenoxide or carbonates such as potassium carbonate.

It will be understood that each unit C in the cyclic oligomer may be the same, or the oligomer may contain different units C of formula (II)

When the units C are different the resulting cocyclics generally have much reduced crystallinity or are completely amorphous which is advantageous in the melt polymerization reactions, since cyclics which have melting points above the polymerization temperature polymerize only with difficulty.

Similarly each unit X in the cyclic oligomer may be the same, or the oligomer may contain different units X of formula —O—R—O— or —S—R—S—.

At the elevated temperatures required for the polymerization the polymers obtained from oligomers containing sulfide linkages react further in a crosslinking reaction to produce insoluble products with increased solvent resistance.

In especially preferred embodiments the cyclic oligomer may contain two different C unit. In other especially preferred embodiments the cyclic oligomer may contain two different X units.

Equation 1

Convenient and efficient pseudo-dilution conditions have been developed, without the need of embploying bisphenols with special geometry that promote cyclic formation. A number of cyclic (aryl ether ketone)s containing the o-dibenzoylbenzene moiety have been synthesized in high yield (Table I, II & III) from the corresponding bisphenol and difluoro-monomers (Equation I). Furthermore, a series of co-cyclic oligomers were prepared when a mixutre of two different difluoro-monomers or two different bisphenols were employed (Table IV, V & VI).

Their cyclic nature has been unambiguously confirmed by a combination of matrix assisted laser desorption mass spectrometry (MALDI-TOF-MS), fast atom bombardment mass spectrometry (FAB-MS), $^1$H NMR, $^{13}$C NMR, FT-IR, reverse phase high pressure liquid chromatography (HPLC) and gel permeation chromatography (GPC) techniques.

The distributiosn of cyclics in the mixtures as revealed by GPC are similar and the yield of cyclic dimers is generally very high. A typical cyclic mixture contain 37% dimer, 15% trimer, 10% tetramer, 6% pentamer, and 30% higher homologues. The preparation of cyclic (aryl ether ketone)s is illustrated by the following examples.

EXAMPLE 1

The cyclization reaction was conducted in a 3 L three-neck round bottom flask which was equipped with a nitrogen inlet, thermometer, Dean-Stark trap, and condenser. The flask was charged with 1.5 L of DMF, 150 mL of toluene, and 150 g of anhydrous potassium carbonate. The solution was mechanically stirred and heated to reflux. The temperature range of the refluxing solution was 145°-8° C. A solution of 4,4'-thiodiphenol (16.26 g, 74 mmol) and 1,2-bis(4-fluorobenzoyl)benzene (24 g, 74 mmol.) in 120 mL of DMF was added over an 8 h period via a syringe pump. After the addition was completed, the resulting solution was refluxed for another 8 h. The reaction mixture was cooled and filtered to remove all the salt. The solvent was then removed fromt he filtrate under reduced pressure. The residue was dissolved in 300 mL of hot chloroform and filtered thorugh a layer of Celite. The chloroform solution was concentrated to 100 mL and added to methanol with vigorous stirring (300 mL) via a dropping funnel. The desired oligomers precipitated as a pale green solid in the methanol, and were collected by filtration. They were then dried in a vacuum oven (120° over 12 h. The yield of 1 was 34 g (90% yield).

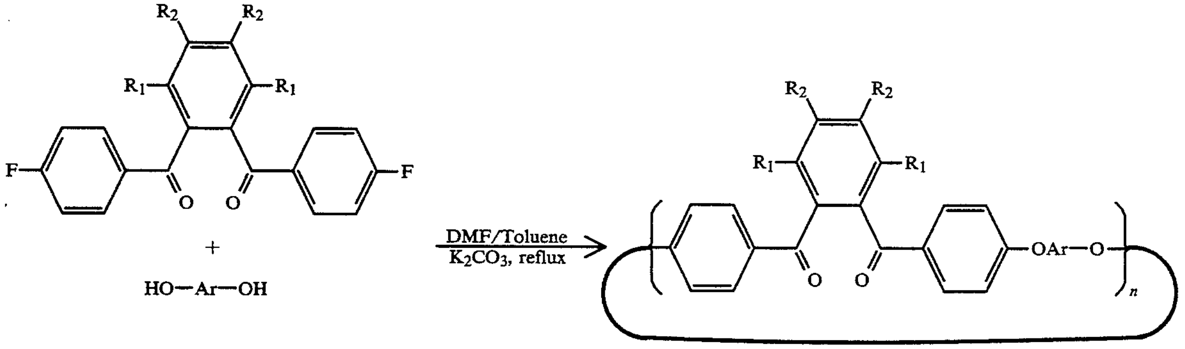

EXAMPLES 2 AND 3

The procedure of example 1 was repeated replacing the thiobisphenol with bisphenol-A and spirobiindane bisphenol.

The following examples are cyclics prepared as in example 1 from the diphenyl-substituted diketone.

TABLE 1

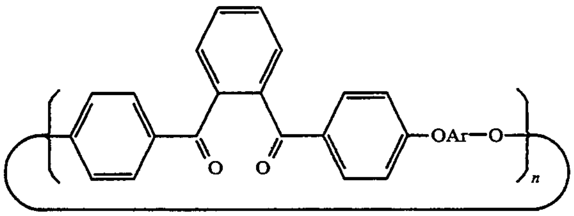

| Example | Ar | Yield[a] % | Mn[b] | Mw[b] | Tg/°C.[d] | Tm/°C[d] | TGA/°C.[e] |
|---|---|---|---|---|---|---|---|
| 1 | 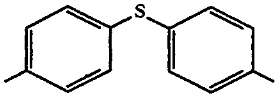 | 85 | 1,300 | 3,100 | 142 (156[c]) | 234 | 476 |
| 2 | 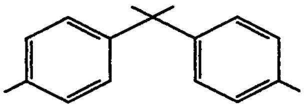 | 85 | 1,500 | 4,800 | 157 (180[c]) | 324 | 452 |
| 3 | 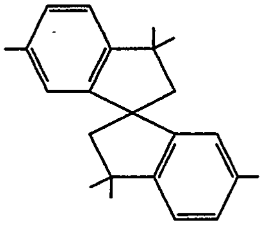 | 80 | 1,000 | 2,100 | 186 (197[c]) | 350 | 481 |

[a]Isolated yield.
[b]Measured by GPC and calibrated against polystyrene standards.
[c]Tg of the corresponding polymer.
[d]Measured on DSC under nitrogen atmosphere (50 mL/min), heating rate was 20° C./min.
[e]Reported for 5% weight loss under nitrogen atmosphere (200 mL/min), and heating rate was 20° C./min.

TABLE II

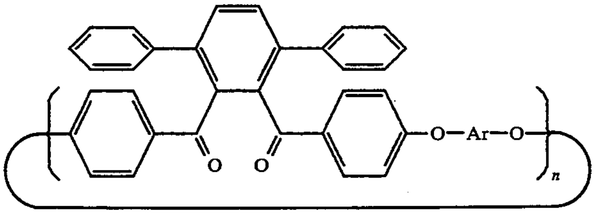

| Example | Ar | Yield[a] % | Mn[b] | Mw[b] | Tg/°C.[d] | Tm/°C[d] | TGA/°C.[e] |
|---|---|---|---|---|---|---|---|
| 4 | 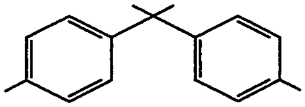 | 80 | 1,900 | 5,300 | 194 (221[c]) | 420 | 480 |
| 5 | 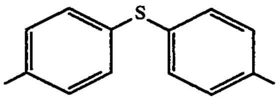 | 90 | 1,900 | 5,700 | 189 (198[c]) | 388 | 462 |

TABLE II-continued

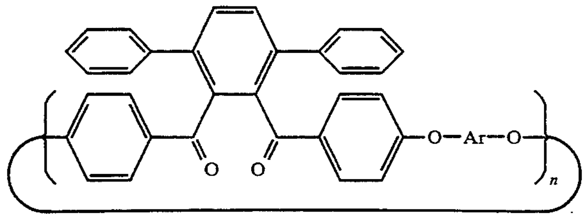

| Example | Ar | Yield[a] % | Mn[b] | Mw[b] | Tg/°C.[d] | Tm/°C[d] | TGA/°C.[e] |
|---|---|---|---|---|---|---|---|
| 6 | 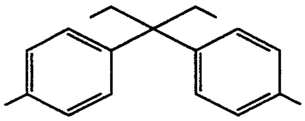 | 68 | 1,500 | 5,400 | 177 | 412 | 483 |
| 7 | 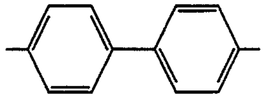 | 35 | 2,300 | 5,900 | 204 (240[c]) | >400 | 507 |
| 8 | 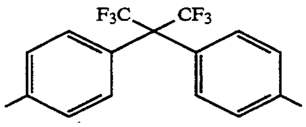 | 95 | 1,700 | 5,800 | 200 | 365 | 526 |
| 9 | 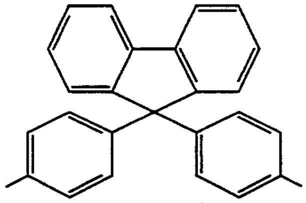 | 80 | 1,400 | 14,400 | 254 | — | 479 |

[a]Isolated yield.
[b]Measured by GPC and calibrated against polystyrene standards.
[c]Tg of the corresponding polymer.
[d]Measured on DSC under nitrogen atmosphere (50 mL/min), heating rate was 20° C./min.
[e]Reported for 5% weight loss under nitrogen atmosphere (200 mL/min), and heating rate was 20° C./min.

The following example is for a cyclic oligomer prepared from the tetraphenyl-substituted diketone.

TABLE III

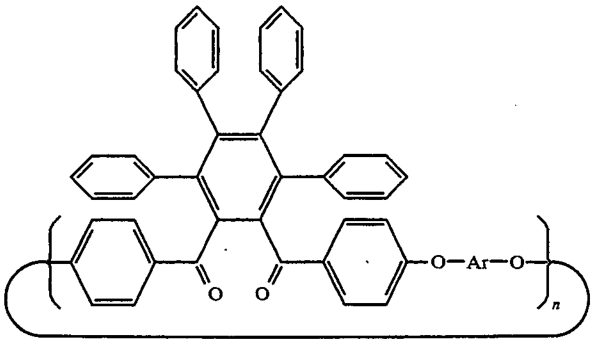

| Example | Ar | Yield[a] % | Mn[b] | Mw[b] | Tg/°C.[d] | Tm/°C[d] | TGA/°C.[e] |
|---|---|---|---|---|---|---|---|
| 10 | 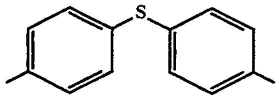 | 90 | 2,400 | 15,000 | 218 | 395 | 452 |

[a]Isolated yield.
[b]Measured by GPC and calibrated against polystyrene standards.
[c]Tg of the corresponding polymer.
[d]Measured on DSC under nitrogen atmosphere (50 mL/min), heating rate was 20° C./min.
[e]Reported for 5% weight loss under nitrogen atmosphere (200 mL/min), and heating rate was 20° C./min.

TABLE IV

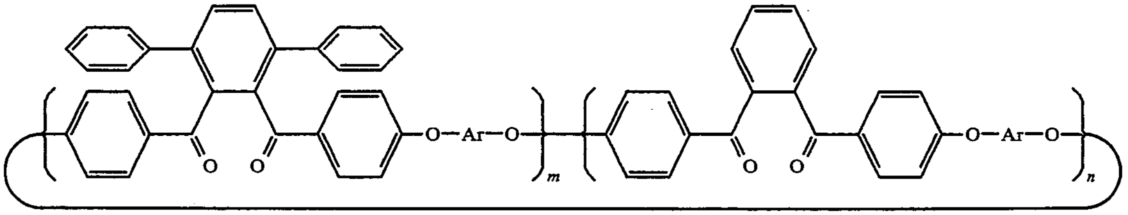

| Example | Ar | m:n | Yield[a] % | Mn[b] | Mw[b] | Tg/°C.[d] | Tm/°C[d] | TGA/°C[e] |
|---|---|---|---|---|---|---|---|---|
| 11 | | 9:1 | 85 | 1,600 | 7,800 | 184 | 367 | 449 |
| 12 | | 3:1 | 85 | 1,900 | 8,900 | 190 | NIL | 475 |
| 13 | 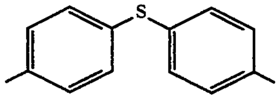 | 1:1 | 85 | 1,500 | 4,800 | 169 | NIL | 455 |
| 14 | | 1:3 | 85 | 1,500 | 5,700 | 162 | NIL | 454 |
| 15 | 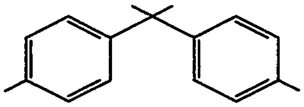 | 1:1 | 85 | 1,400 | 5,400 | 180 | NIL | 473 |

[a]Isolated yield.
[b]Measured by GPC and calibrated against polystyrene standards.
[c]Tg of the corresponding polymer.
[d]Measured on DSC under nitrogen atmosphere (50 mL/min), heating rate was 20° C./min.
[e]Reported for 5% weight loss under nitrogen atmosphere (200 mL/min), and heating rate was 20° C./min.

The following are examples of cocyclics obtained as in example 1 by using a combination of two of the diketones.

Cyclic oligomers 1-3 and co-cyclic 11-15 were found to be soluble in chloroform, THF and DMSO. On the other hand cyclics 4-6 were much less soluble. All of them have moderate softening temperature. All homocyclic oligomers 1-3 & 4-7 exhibit a melting point, which is due to the dimer. Cyclic oligomers 4-7 have much higher Tm (>390° C.) compared to 1-3. Cocyclics 11-15 are totally amorphous with no detectable melting point The following cocyclics were synthesized by using a mixture of two different bisphenols in the preparation according to example 1.

The following examples are cocyclics in which half of the orthodibcnzoyldiketone has been replaced with the bcnzophenonc moiety.

TABLE V

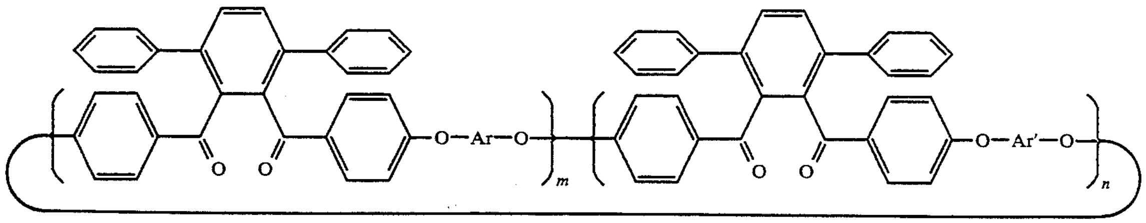

| Example | Ar | Ar' | Yield[a] % | Mn[b] | Mw[b] | Tg/°C.[d] | Tm/°C[d] | TGA/°C[e] |
|---|---|---|---|---|---|---|---|---|
| 16 | | 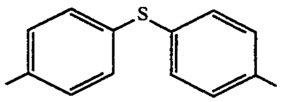 | 85 | 1,600 | 8,500 | 195 | NIL | 450 |
| 17 | 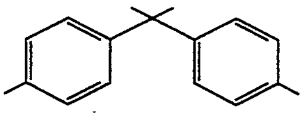 | 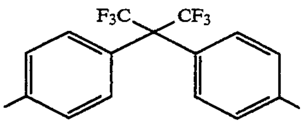 | 95 | 1,700 | 6,800 | 201 | 354 | 528 |
| 18 | | 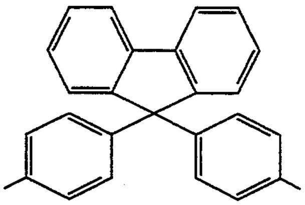 | 95 | 1,700 | 6,200 | 219 | NIL | 461 |

[a]Isolated yield.
[b]Measured by GPC and calibrated against polystyrene standards.
[c]Tg of the corresponding polymer.
[d]Measured on DSC under nitrogen atmosphere (50 mL/min), heating rate was 20° C./min.
[e]Reported for 5% weight loss under nitrogen atmosphere (200 mL/min), and heating rate was 20° C./min.

TABLE VI

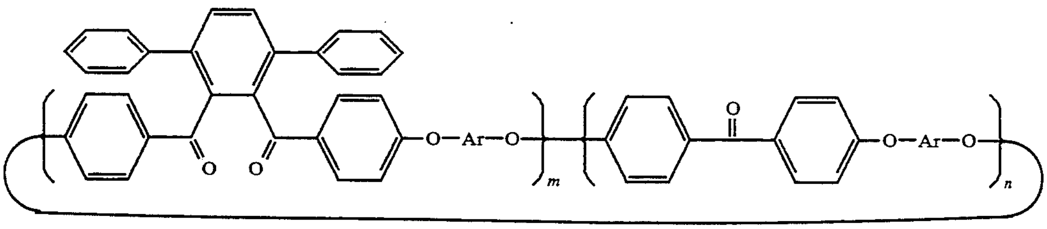

| Example | Ar | m:n | Yield[a] % | Mn[b] | Mw[b] | Tg/°C.[d] | Tm/°C[d] | TGA/°C[e] |
|---|---|---|---|---|---|---|---|---|
| 19 | 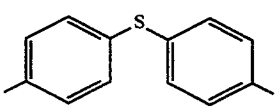 | 1:1 | 85 | 1,300 | 4,500 | 175 | 359 | 457 |

TABLE VI-continued

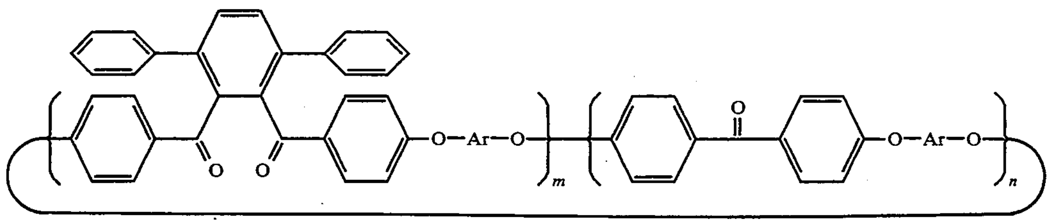

| Example | Ar | m:n | Yield[a] % | Mn[b] | Mw[b] | Tg/°C.[d] | Tm/°C[d] | TGA/°C[e] |
|---|---|---|---|---|---|---|---|---|
| 20 | 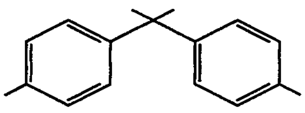 | 1:1 | 75 | 1,700 | 8,600 | 180 | NIL | 473 |

[a]Isolated yield.
[b]Measured by GPC and calibrated against polystyrene standards.
[c]Tg of the corresponding polymer.
[d]Measured on DSC under nitrogen atmosphere (50 mL/min), heating rate was 20° C./min.
[e]Reported for 5% weight loss under nitrogen atmosphere (200 mL/min), and heating rate was 20° C./min.

The cyclic oligomers containing aromatic sulfide linkages can be oxidized to the corresponding sulfones thus providing a new class of cyclics.

Cyclic (aryl ether phthalazine) oligomers can be synthesized from the corresponding diketone cyclics by reaction with hydrazinc.

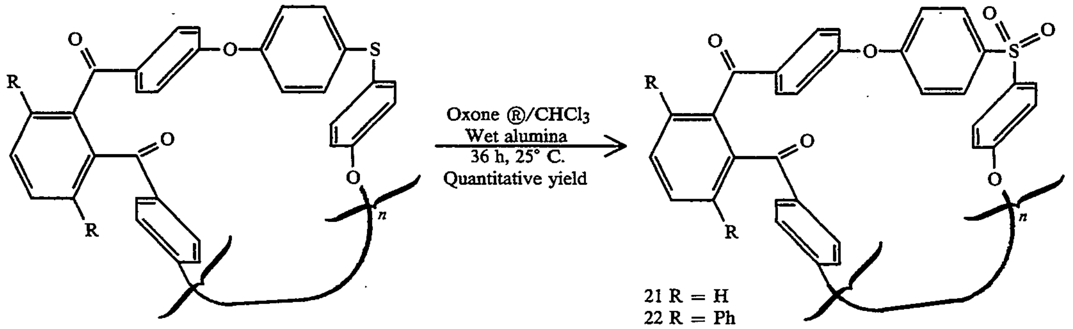

21 R = H
22 R = Ph

EXAMPLE 21

Cyclic oligomer 5 (1 g, 2 mmol.) was added to a vigorously stirred suspension of wet alumina (3 g ) and Oxone ® (4.92 g, 8 mmol.) in chloroform (25mL). The mixture was reftaxed for about 36 h. The mixture was filtered and the residue was rinsed with another 5 mL of chloroform. The flitrate was evaporated to give the desired sulfone cyclic oligomer 21 in quantitative yield. (Wet alumina was prepared by adding water (10 mL) to alumina (50 g; Brockman grade I, 200 mesh; Aldrich Chemical Company)).

Physical Properties of the Sulfone Cyclic Oligomers

| Example | Yield/%[a] | Mn[b] | Mw[b] | Tg/°C.[c] | TGA/°C.[d] |
|---|---|---|---|---|---|
| 21 | 100 | 1,500 | 3,500 | 190 | 500 |
| 22[f] | 100 | 1,600 | 2,400 | 230 | 520 |

Isolated yield.
Measured by GPC and calibrated against polystyrene.
Measured on DSC under nitrogen atmosphere(50 mL/min), and heating rate was 20° C./min.
Reported for 5% weight loss under nitrogen atmosphere(200 mL/min.), and heating rate was 20° C./min.
The starting material has Mn = 1,400, Mw = 1,800.

EXAMPLE 23

Cyclic oligomer 3 (16 g) was refluxed with 50 mL of chloroform for 30 min. Then the solution was allowed to stand at room temp for 2 h. At this time the cyclic monomer (n=1) precipitated out and was removed by suction filtration. Evaporation of the tiltrate ;gave the desired oligomer mixture( 6.5 g) containing 8% (w/w) of cyclic monomer.

To a solution of cyclic oligomer 3 (2 g) in dioxane (20 mL) was added hydrazine hydrate (2 mL) and conc. HCl acid (0.6 mL). The resulting solution was refluxed for 3 h. A green solid precipitated out during the reflux. The solid was filtered, redissolved in acetic acid (20 mL), followed by sodium nitrite (3 g) to remove any hydrazone formed. The solution was refluxcd until no more nitrogen dioxiae was evolved. The solution was coagulated in water (20 mL) and filtered, redissoived in chloroform, and filtered. The chloroform solution was concentrated and then coagulated in methanol (50 mL). The green solid was filtered and dried under vacuum at 120° C. overnight to give the desired product 23 in 90% yield.

TABLE VII

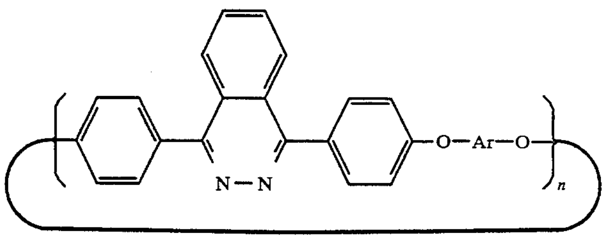

| Example | Ar | Yield[a] % | Mn[b] | Mw[b] | Tg/°C.[d] | Tm/°C[d] | TGA/°C.[e] |
|---|---|---|---|---|---|---|---|
| 23 | 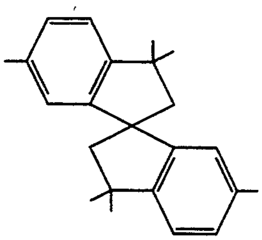 | 90 | 1,800 | 3,800 | 230 (250[c]) | nil | 420 |
| 24 | 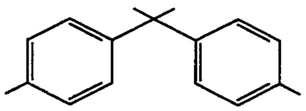 | 80 | — | — | 217 (215[c]) | Not Detected | 450 |

[a]Isolated yield.
[b]Measured by GPC and calibrated against polystyrene standards.
[c]Tg of the corresponding polymer.
[d]Measured on DSC under nitrogen atmosphere (50 mL/min), heating rate was 20° C./min.
[e]Reported for 5% weight loss under nitrogen atmosphere (200 mL/min), and heating rate was 20° C./min.

Cyclic (aryl ether isoquinoline) oligomers can also be synthesized by reaction of the corresponding diketone cyclic with benzylamine.

EXAMPLE 25

To a solution of 8 (0.5 g) in chlorobenzene (10 mL) was added benzylamine (2 mL)and 1,8-diazabicyclo[5.4.0]undec-7-ene (2 mL). The resulting solution was refluxed for 30 h. The solution was coagulated in methanol (50 mL), filtered to give 25 as a green solid in 80% yield.

TABLE VIII

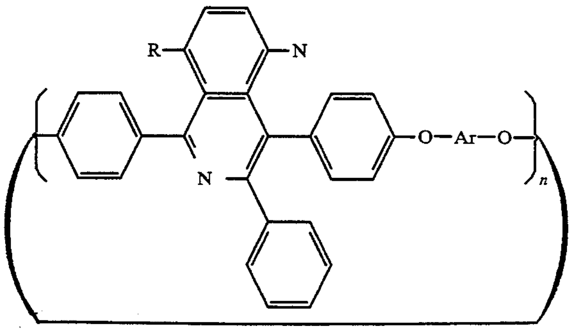

| Example | R | Ar | Yield[a] % | Mn[b] | Mw[b] | Tg/°C.[d] | Tm/°C.[d] | TGA/°C.[e] |
|---|---|---|---|---|---|---|---|---|
| 25 | H | 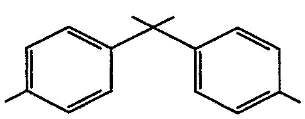 | 85 | — | — | 211 (226[c]) | Not Detected | 530 |

TABLE VIII-continued

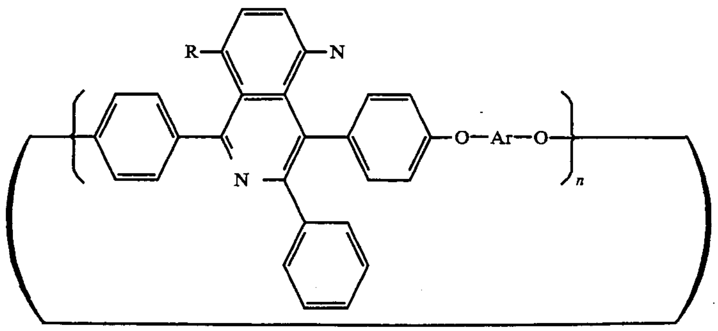

| Example | R | Ar | Yield[a] % | Mn[b] | Mw[b] | Tg/°C.[d] | Tm/°C.[d] | TGA/°C.[e] |
|---|---|---|---|---|---|---|---|---|
| 26 | Ph | 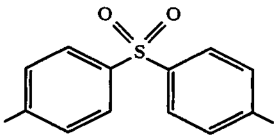 | 80 | 2,700 | 3,100 | 228 | NIL | 431 |

[a]Isolated yield.
[b]Measured by GPC and calibrated against polystyrene standards.
[c]Tg of the corresponding polymer.
[d]Measured on DSC under nitrogen atmosphere (50 mL/min), heating rate was 20° C./min.
[e]Reported for 5% weight loss under nitrogen atmosphere (200 mL/min), and heating rate was 20° C./min.

Polymerization of Cyclic (Aryl Ether Ketone) Oligomers

EXAMPLE 27

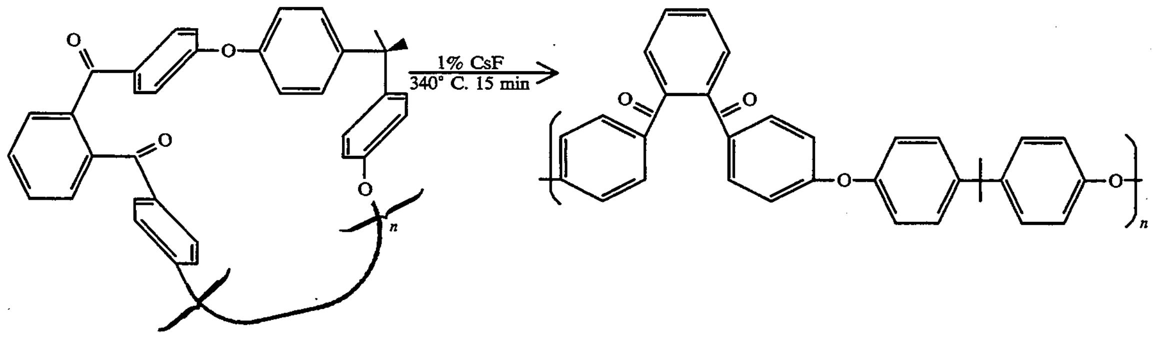

To a chloroform solution (10 mL) of cyclic oligomer from example 2 (1 g, 1.96 mmol), a methanolic solution of CsF (670 mL, conc.=4.4.mg/mL, 0.0196 mmol.) was added, and the solvent was evaporated under reduced pressure. The solid was dried at 140° C. for 6 h under vacuum.

The resulting solid was heated under nitrogen atmosphere at 340° C. for 15 min. The product was then analyzed by GPC, and was found to be high molecular weight material (Mw=165,000 g/mol).

EXAMPLE 28

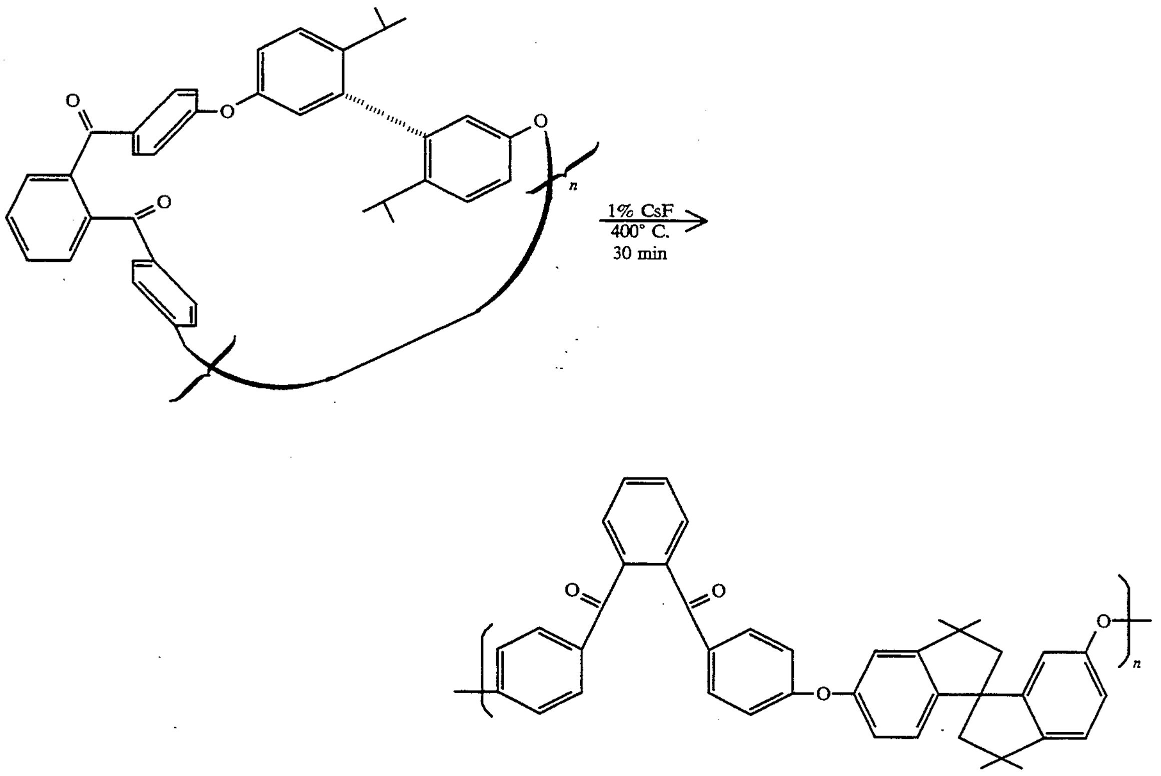

The cyclic oligomer from example 3 was polymerized, as in example 27 in the presence of 1% CsF for 30 min at 400° C. After this time 30% of the cyclic monomers remained. The weight average molecular weight was 180,000 and the number average molccular weight was 1,800. This indicates that the SBI containing cyclics do not polymerize completely because of the stability of the cyclics.

EXAMPLE 29

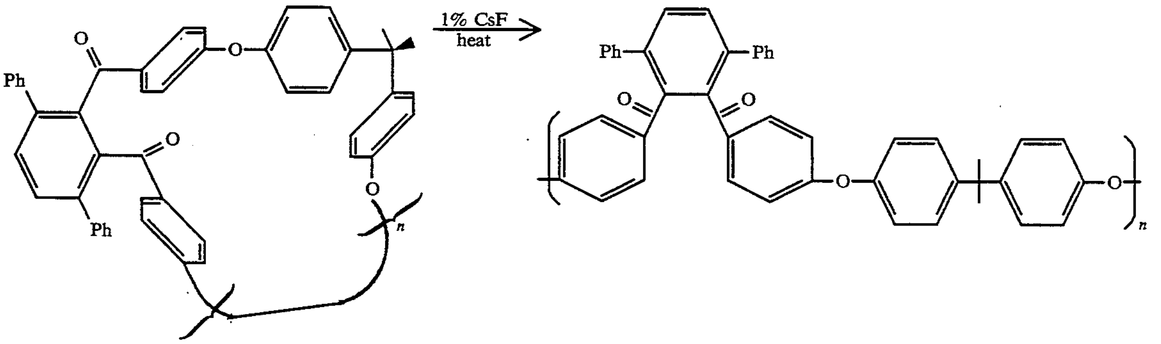

The cyclic oligomer from example 4 was polymerized as in example 27 in the presence of 1% CsF at various temperature for 30 min.

| Temperature °C. | Mw |
|---|---|
| 280 | 5,000 |
| 300 | 12,000 |
| 320 | 32,000 |
| 340 | 65,000 |
| 360 | 190,000 |
| 380 | 370,000 |

-continued

The dimer cyclic has a reciting point of 420° C. At the lower temperatures cyclic dimer remains. When these cyclic oligomers are polymerized in solution in dimethylacctamide at the temperature of reflux for 4 hours in the presence of potassium carbonate as catalyst high molecular weight polymer is obtained with only a trace of cyclic remaining.

EXAMPLE 30

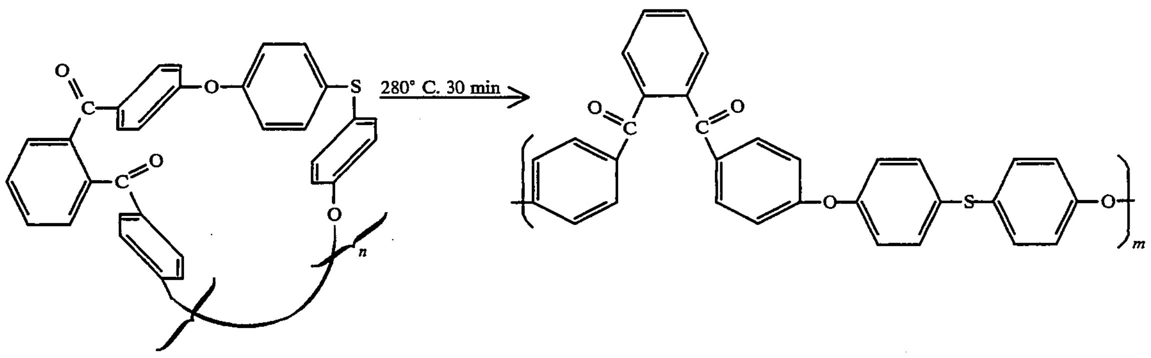

The sulfide containing cyclic oligomer of example 1 (100 mg) was heated under nitrogen atmosphere as in Example 29 at 280° C. for 30 min. The color of the sample changed from pale green to amber, and the Tg rose to 156° C., a 14° C. increase compared to the starting oligomer 1. GPC analysis on the product indicated that it was high molecular weight material (Mw=446,000 g/mol, Mn=20,000 g/mol) and only a small amount of cyclic material remained.

EXAMPLE 31

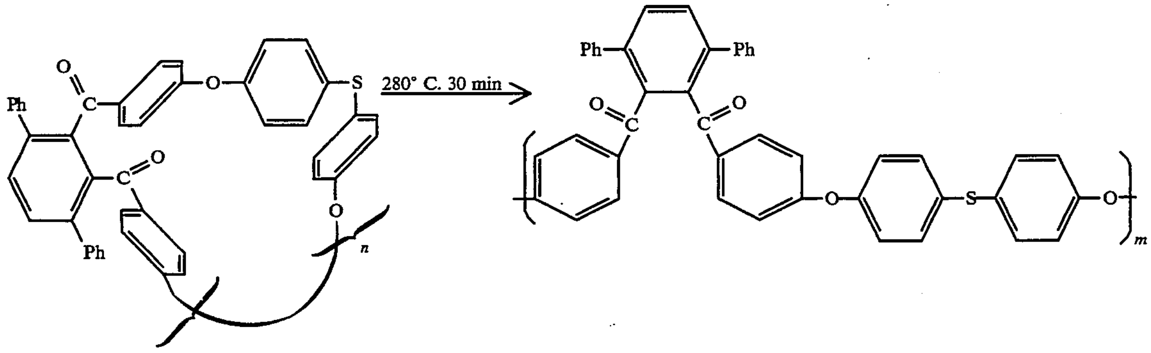

The cyclic oligomer from example 5 was polymerized as in example 30 at various temperatures for 30 minutes under nitrogen.

| Curing T, °C. | % soluble in $CHCl_3$ |
|---|---|
| as prepared | 100 |
| 280 | 81 |
| 300 | 69 |
| 320 | 36 |
| 340 | 19 |
| 360 | 15 |
| 380 | 2 |

This example illustrates that tim sulfide containing cyclics polymerize and then undergo further crosslinking reactions to become insoluble. The cyclic dimer in this case has a melting point of 350° C., therefore higher temperatures are necessary to complete the polymerization reaction.

EXAMPLE 32

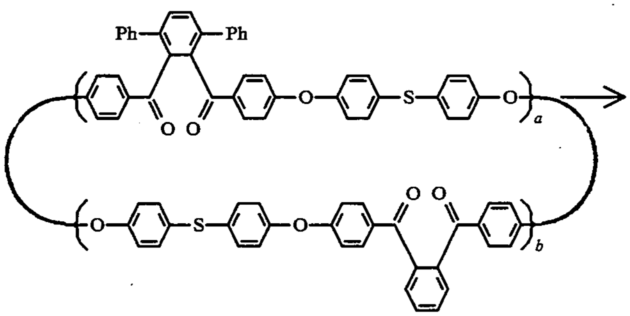

Tg = 190° C. a:b = 3:1

-continued

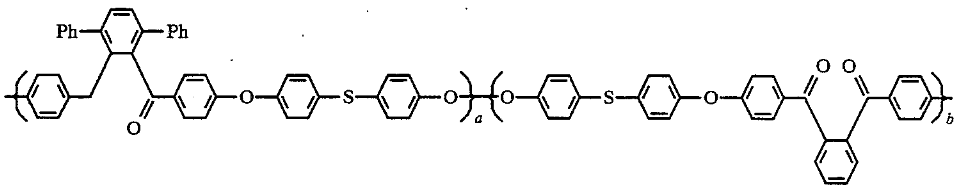

The cocyclic from example 12 was polymerized as in example 30 at the following temperatures for 30 minutes under nitrogen.

| Curing T, °C. | % soluble in $CHCl_3$ |
|---|---|
| as prepared | 100 |
| 320 | 100 |
| 330 | 88 |
| 340 | 54 |
| 350 | 27 |
| 370 | 6 |

The cocyclic does not have a melting point but has a Tg of 190° C.

We claim:

1. A cyclic oligomer of formula (I):

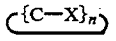

(I)

wherein n is an integer of 2 to 20 and in which eacH C in the oligomer is a radical of formula (II):

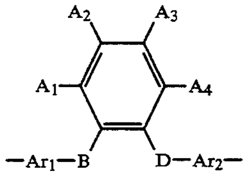

(II)

and each X in the oligomer is a radical of formuia —O—R—O— or —S—R—S—, in which $A_1$, $A_2$, $A_3$ and $A_4$ are each independently selected from hydrogen, aryl selected from the group consisting of phenyl, naphthyl and anthracyl, diphenylether or heteroaromatic radicals selected from the group consisting of pyridinyl, pyrarzinyl, quinolinyl, thiophenyl, benzothiophenyl, furanyl and dibenzofuranyl, said aryl, diphenylether and heteroaromatic radicals being unsubstituted or substituted by a substituent selected from lower alkyl of 1 to 6 carbon atoms, lower alkoxy of 1 to 6 carbon atoms, lower thioalkyl of 1 to 6 carbon atoms, halogen, phenyl, naphthyl, anthracyl, diphenylether or heteroaromatic radicals selected from the group consisting of pyridinyl, pyrazinyl, quinolinyl, thiophenyl, benzothiophenyl, furanyl and dibenzofuranyl, B and D are both carbonyl groups CO, or B and D together represent a divalent radical of formula:

—C=N—N=C— (III)

or

-continued

—C=N—C=C— (IV)
$Ar_3$ wherein $Ar_3$ is an aryl selected from the group consisting of phenyl, naphthyl and anthracyl, diphenylether or heteroaromatic radical selected from the group consisting of pyridinyl, pyrazinyl, quinolinyl, thiophenyl, benzothiophenyl, furanal and dibenzofuranyl, unsubstituted or substituted by a substituent selected from lower alkyl of 1 to 6 carbon atoms, lower alkoxy of 1 to 6 carbon atoms, lower thioalkyl of 1 to 6 carbon atoms, halogen, phenyl, naphthyl; anthracyl, diphenylether or heteroaromatic radicals selected from the group consisting of pyridinyl, pyrazinyl, quinolinyl, thiophenyl, benzothiophenyl, furanyl and dibenzofuranyl, $Ar_1$ and $Ar_2$ are each phenylene radicals, unsubstituted or substituted 1 to 4 times by a substituent selected from lower alkyl of 1 to 6 carbon atoms, lower alkoxy of 1 to 6 carbon atoms, lower thioalkyl of 1 to 6 carbon atoms, halogen, phenyl, naphthyl, anthracyl, diphenylether or heteroaromatic radicals selected from the group consisting of pyridinyl, pyrazinyl, quinolinyl, thiophenyl, benzothiophenyl, furanyl and dibenzofuranyl, R is arylene selected from the group consisting of phenylene, naphthylene, anthracylene, thiobisphenyl, sulfonylbisphenyl and alkylidinylbisphenyl of formula —Ph—$R_1$—Ph— which $R_1$ is a straight chain or branched alkylene of 1 to 6 carbon atoms and Ph is phenylene, in which each arylene and phenylene moiety is unsubstituted or substituted by lower alkyl of 1 to 6 carbon atoms, lower alkoxy of 1 to 6 carbon atoms, lower thioalkyl of 1 to 6 carbon atoms, halogen, phenyl, naphthyl, anthracyl, diphenylether or heteroaromatic radicals selected from the group consisting of pyridinyl, pyrazinyl, quinolinyl, thiophenyl, benzothiophenyl, furanyl and dibenzofuranyl, and the alkylidine moiety of said aralkylidinylphenylene is unsubstituted or fluoro-substituted alkylidine.

2. A cyclic polyketone oligomer of claim 1, wherein B and D are both carbonyl groups.

3. A cyclic polyketone oligomer of claim 2, wherein X is —O—R—O—, and R is selected from dimethylmethylidinylbisphenol, diethylmethylidinylbisphenyl, biphenylene, thiobisphenyl and di-tri-fluoromethylidinylbisphenyl.

4. A cyclic polyketone oligomer of claim 3, wherein $Ar_1$ and $Ar_2$ are both phenylene and $A_1$, $A_2$, $A_3$ and $A_4$ are independently selected from hydrogen and phenyl.

5. A cyclic polyphthalazine of claim 1, wherein B and D represent said divalent radical of formula (III) whereby B and D form part of a pyridazine ring.

6. A cyclic polyphthalazine of claim 5, wherein $A_1$ and $Ar_2$ are both phenylene; $A_1$, $A_2$, $A_3$ and A4 are all hydrogen; and X is —O—R—O—, in which R is spirobiindanebisphenyl or dimethylmethylidinylbisphenyl.

7. A cyclic polyisoquinoline of claim 1, wherein B and D represent said divalent radical of formula (IV) whereby B and D form part of a pyridine ring.

8. A cyclic polyisoquinoline of claim 7, wherein $A_1$ and $Ar_2$ are both phenylene; $A_1$, $A_2$, $A_3$ and $A_4$ are independently selected from hydrogen and phenyl; and X is —O—R—O—, wherein R is dimethylmethylidinylbisphenyl or sulfonylbisphenyl.

9. A cyclic oligomer according to claim 1, which contains two different radicals C of said formula (II).

10. A cyclic oligomer according to claim 1, which contains two different radicals X.

11. A process for the preparation of a linear high molecular weight polymer which comprises ring-open polymerizing a cyclic oligomer, as defined in claim 1 at an elevated temperature in the presence of a catalyst.

12. A process according to claim 11, wherein said ring-open polymerizing is carried out in a solvent.

13. A process according to claim 11, wherein said ring-open polymerizing is carried out in a melt of the oligomer.

14. A process for producing a cyclic oligomer of formula (I), as defined in claim 1, comprising:

reacting a di-carbonyl compound of formula (V):

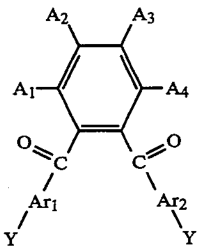

(V)

with a compound of formula (VI):

$$HZ—R—ZH \quad (VI)$$

in a solvent under high dilution conditions such that reactive end groups Y and ZH are present in a low concentration, to produce a cyclic oligomer of formula (I), wherein B and D both carbonyl groups, wherein $A_1$, $A_2$, $A_3$, $A_4$, $Ar_1$, $Ar_2$ and R are as defined in claim 1, each Y is selected from fluoro and chloro and each Z is selected from O or S.

15. A process according to claim 14, including reacting the product cyclic oligomer of formula (I), in which B and D are both carbonyl groups, with hydrazine to produce a cyclic oligomer of said formula (I), in which B and D represent said divalent radical of formula (III), whereby B and D form part of a pyridazine ring.

16. A process according toclaim 14, including reacting the product cyclic oligomer of formula (I), in which B and D are both carbonyl groups with benzylamine to produce a cyclic oligomer of said formula (I), in which B and D represent said divalent radical of formula (IV), whereby B and D form part of a pyridine ring.

* * * * *

UNITED STATES PATENT AND TRADEMARK OFFICE

CERTIFICATE OF CORRECTION

PATENT NO. : 5,405,956

DATED : April 11, 1995

INVENTOR(S) : Allan S. Hay and Kwok P. Chan

It is certified that error appears in the above-identified patent and that said Letters Patent is hereby corrected as shown below:

At column 2, line 62, delete "quinovlinyl" and insert therefor ...quinolinyl...;

At column 4, line 31, delete "Still" and insert therefor ...still...;

At column 4, line 47, delete "iinear" and insert therefor ...linear...;

At column 5, line 51, delete "unit" and insert therefor ...units...;

At column 16, line 52, delete "tiltrate" and insert therefor ...filtrate...;

At column 16, line 62, delete "dioxiae" and insert therefor ...dioxide...;

At column 16, line 63, delete "redissoived" and insert therefor ...redissolved...;

At column 22, line 41, delete "reciting" and insert therefor ...melting...;

At column 24, line 27, delete "tim" and insert therefor ...the...;

At column 25, line 31, delete "eacH" and insert therefor ...each...;

At column 25, line 49, delete "pyrarzinyl" and insert therefor ...pyrazinyl... .

Signed and Sealed this

Tenth Day of October, 1995

Attest:

Bruce Lehman

BRUCE LEHMAN

*Attesting Officer* *Commissioner of Patents and Trademarks*